United States Patent [19]
Sodroski et al.

[11] Patent Number: 5,981,276
[45] Date of Patent: Nov. 9, 1999

[54] VECTORS CONTAINING HIV PACKAGING SEQUENCES, PACKAGING DEFECTIVE HIV VECTORS, AND USES THEREOF

[75] Inventors: Joseph G. Sodroski, Medford; William A. Haseltine; Mark Poznansky, both of Cambridge, all of Mass.; Andrew Lever, Pinner, United Kingdom

[73] Assignee: Dana-Farber Cancer Institute, Boston, Mass.

[21] Appl. No.: 08/915,429

[22] Filed: Aug. 20, 1997

Related U.S. Application Data

[62] Division of application No. 08/152,902, Nov. 15, 1993, Pat. No. 5,665,577, which is a continuation of application No. 07/827,588, Jan. 29, 1992, abandoned, which is a continuation of application No. 07/540,746, Jun. 20, 1990, abandoned.

[51] Int. Cl.$^6$ ............................ C12N 15/86; C12N 15/49; C12N 5/10
[52] U.S. Cl. ............................ 435/320.1; 435/455
[58] Field of Search ............................ 435/320.1, 172.3, 435/455

[56] References Cited

U.S. PATENT DOCUMENTS

| | | | |
|---|---|---|---|
| 5,081,029 | 1/1992 | Zarling et al. | 435/325 |
| 5,614,404 | 3/1997 | Mazzara et al. | 435/236 |
| 5,665,577 | 9/1997 | Sodroski et al. | 435/456 |

FOREIGN PATENT DOCUMENTS

WO 87/02038   4/1987   WIPO .

OTHER PUBLICATIONS

Feinberg et al., AIDS Res. and Human Retrovir. 8(6): 1013–1022 (1992).
Gilboa et al., Trends in Genetics 10(4):139–144 (1994).
New Scientist 146(1977):36–40 (1995).
M.I. Johnston et al., (1993), Science 260:1286–1293.
A.G. Fisher et al., (1985) Nature 316:262–265.
D. Baltimore (1988) nature 335:395–396.
Marjman et al., Nature 318:414 (Dec. 5, 1985).
M.H. Malin et al., Cell 58:205 (Jul. 14, 1989).
M.A. Adam et al., Journal of Virol 62:3802 (Oct. 1988).
Barre–Sinoussi et al., Science 220:868–871 (1983).
Gallo et al., Science 224:500–503 (1984).
Levy et al., Science 840–842 (1984).
Popovic et al., Science 224: 497–500 (1984).
Sarngadharan et al., Science 224: 506–508 (1984).
Siegel et al., N.Engl. J. Med. 305:1439–1444 (1981).
Zagury et al., Science 231:850–853 (1986).
Ratner et al., Nature 313:277–284 (1985).
Sanchez–Pescador et al., Science 227:484–492 (1985).
Muesing et al., Nature 313:450–457 (1985).
Wain–Hobson et al., Cell 40:9–17 (1985).
Guyader, M. et al., Nature 326:662–669 (1987).
Chakabarti, L. et al., Nature 328:543–547 (1987).
Haase, Nature 322:130–136 (1986).
Coffin, J. Gen. Virol. 42:1–26 (1979).
Haseltine, Journ. of Acquired Immune Deficiency Syndrome 1:217–240 (1988).
Sodroski et al., Science 231:1549–1553 (1986).
Arya et al., Science 229:69–73 (1985).
Sodroski et al., Science 227:171–173 (1985).
Sodroski et al., Nature 321:412–417 (1986).
Feinberg et al., Cell 46:807–817 (1986).
Wong–Staal et al., AIDS Res. 7 Human Retroviruses 3:33–39 (1987).
Rosen et al., Nature 319:555–559 (1986).
Dayton et al., Cell 44:941–947 (1986).
Bender et al., J. Virol 61:1639–1646 (1987).
Katz et al., J. Virol. 59:163–167 (1986).
Mann et el., Cell 33:153–159 (1983).
Pugatsch et al., Virology 128:505–511 (1983).
Watanabe et al., PNAS 79:5986–5990 (1983).
Eglitis et al., Bio Techniques 6:608–614 (1988).
Adam et al., J. Virol. 62:3802–3806 (1988).
Cornetta, Prog. in Nucleic Acids Res. & Mol. Biol. 36:311–322 (1989).
Joyner, Nature 305:556–558 (1983).
Gilboa, Biotechniques 4:504–512 (1986).
E.C.M. Mariman, Nature 318:414 (1985).
R.Teller et al., Nature 318:414 (1985).
M.H. Malim et al., Cell 58:205–214 (1989).
A.Aldovini et al., J.Virology 64:1920–1926 (1990).
A.Lever et al., J.Virology 63:4085–4087 (1989).
A.D. Miller et al., Mol. Cell. Biol. 6:2895–2902 (1986).
D. Markowitz et al., Virology 167:400–406 (1988).

*Primary Examiner*—Johnny F. Railey, II
*Attorney, Agent, or Firm*—Ronald I. Eisenstein; David S. Resnick

[57] ABSTRACT

Packaging defective and packaging proficient HIV vectors are disclosed. These vectors can be used to establish HIV packaging defective cell lines, and to package desired genes. These cell lines can be used in developing a vaccine, HIV antibodies and as part of a system for gene transfer. The packaging proficient vector can be used to target HIV target cells.

11 Claims, 7 Drawing Sheets

VECTORS CONTAINING HIV PACKAGING SEQUENCES, PACKAGING DEFECTIVE HIV VECTORS, AND USES THEREOF

This is a divisional of application Ser. No. 08/152,902 filed Nov. 15, 1993, now U.S. Pat. No. 5,665,577, which is a continuation of Ser. No. 07/827,588 filed Jan. 29, 1992, now abandoned, which was a continuation of Ser. No. 07/540,746 filed Jun. 20, 1990, now abandoned.

The present invention is directed to vectors including vectors comprising a packaging defective HIV provirus, a vector comprising a HIV packaging sequence and a gene to be transferred, the use of the packaging defective vectors to create HIV packaging defective cell lines, and the uses of the vectors and cell lines. Most preferably, the HIV provirus is an HIV-1 provirus.

The human immunodeficiency virus (HIV-I, also referred to as HTLV-III, LAV or HTLV-III/LAV) is the etiological agent of the acquired immune deficiency syndrome (AIDS) and related disorders [Barre-Sinoussi, et al., *Science* 220:868–871 (1983); Gallo et al, *Science* 224:500–503 (1984); Levy et al., *Science* 225:840–842 (1984); Popovic et al., *Science* 224:497–500 (1984); Sarngadharan et al., *Science* 224:506–508 (1984); Siegal et al., *N. Engl. J. Med.* 305:1439–1444 (1981)]. The disease is characterized by a long asymptomatic period followed by progressive degeneration of the immune system and the central nervous system. Studies of the virus indicate that replication is highly regulated, and both latent and lytic infection of the CD4 positive helper subset of T-lymphocytes occur in tissue culture [Zagury et al., *Science* 231:850–853 (1986)]. The expression of the virus in infected patients also appears to be regulated to enable evasion of the immune response. Molecular studies of the regulation and genomic organization of HIV-I show that it encodes a number of genes [Ratner et al., *Nature* 313:277–284 (1985); Sanchez-Pescador et al., *Science* 227:484–492 (1985); Muesing et al., *Nature* 313:450–457 (1985); Wain-Hobson et al., *Cell* 40:9–17 (1985)]. The other primate immunodeficiency viruses, HIV-2 and simian immunodeficiency virus (SIV) also share many of the same structural and regulatory genes such as gag, pol, env, tat, rev and nef [Guyader, M., et al., *Nature* 326:662–669 (1987); Chakrabarti, L., et al., *Nature* 328:543–547 (1987), which are incorporated herein by reference].

Retroviruses are typically classified as belonging to one of three subfamilies, namely oncoviruses, spumaviruses and lentiviruses. Infection by oncoviruses is typically associated with malignant disorders. These viruses typically contain a single-stranded, plus-strand RNA genome of approximately 8,000 to 10,000 nucleotides encompassing the gag, pol and env, genes, as well as long terminal repeat (LTR) sequences. Oncoviruses typically contain an oncogene. It is generally believed that spumaviruses are not pathogenic in vivo, although they induce foamy cytopathic changes in tissue culture. Infection by lentiviruses is generally slow and causes chronic debilitating diseases after a long latency period. These viruses, in addition to the gag, pol, and env genes possess a number of additional genes with regulatory functions.

The human immunodeficiency viruses (HIV) has been classified as a lentivirus, because it too causes slow infection and has structural properties in common with such viruses. [See Haase, A. T., *Nature* 322: 130–136 (1986)].

All known retroviruses share features of the replicative cycle, including packaging of viral RNA into virions, entry into target cells, reverse transcription of viral RNA to form the DNA provirus, and stable integration of the provirus into the target cell genome [Coffin, J., *J. Gen. Virol.* 42:1–26 (1979)]. Replication-competent proviruses, at a minimum, contain regulatory long terminal repeats (LTRs) and the gag, pro, pol, and env genes which encode core proteins, a protease, reverse transcriptase/RNAse H/integrase and envelope glycoproteins, respectively [J. Gen. Virol. 42, supra]. The LTRs contain cis-acting sequences important for integration, transcription and polyadenylation.

HIV shares the pg, pro, pol and env genes, respectively with other retroviruses [Haseltine, W. A., *Journal of Acquired Immune Deficiency Syndrome*, 1:217–240 (1988)]. HIV also possesses additional genes modulating viral replication. The HIV-1 genome encodes vif, vpr, tat, rev, vpu and nef proteins [Haseltine, W. A., Journal of Acquired Immune Deficiency Syndrome, supra]. Additionally, the long terminal repeats (LTRs) of HIV contain cis-acting sequences that are important for integration, transcription and polyadenylation. Additional cis-acting signals allow regulation of HIV sequences by some of the novel HIV gene products, (Haseltine, W. A., Journal of Acquired Immune Deficiency Syndrome, supra). Sodroski et al., *Science* 231:1549–1553 (1986); Arya et al., *Science* 229:69–73 (1985); Sodroski et al., *Science* 227:171–173 (1985); Sodroski et al., *Nature* 321:412–417 (1986); Feinberg et al., *Cell* 46:807–817 (1986) Wong-Staal et al, *AIDS Res. and Human Retroviruses* 3: 33–39 (1987); which are all incorporated herein by reference]. The region between the 5' major splice donor and the gag gene initiation codon is highly conserved in different HIV-1 strains sequenced to date [Myers, G., et al, *Theoretical Biology and Biophysics,* (1988)].

Most of these genes encode products that are necessary for the viral life cycle. For example, the tat gene encodes a 14kD protein that is critical for HIV replication and gene expression [Rosen, C. A., et al., *Nature* 319:555–559 (1986); Sodroski, J. et al., *Science* 227:171–173 (1985); Arya et al, *Science* 229: supra, Sodroski, et al., *Science* 229, supra and Dayton, A., et al., *Cell* 44:941–497 (1986) which are all incorporated herein by reference]. Another gene necessary for replication is the rev gene. [Sodroski, et al., *Nature* 321:412–417 (1986), which is both incorporated herein by reference].

In some oncoviruses, cis-acting sequences located between the 5' LTR and the gag gene initiation codon have been located which are necessary for the efficient packaging of the viral RNA into virions [Bender, M. A., et al, *J. Virol* 61:1639–1646 (1987), Katz, R. A., et al, *J. Virol* 59:163–167 (1986), Mann, R., et al, *Cell* 33:153–159 (1983), Pugatsch, T., et al, *Virology* 128:505–511 (1983), Watanabe, S., et al, *Proc. Natl. Acad. Sci.* 79:5986–5990 (1983) Eglitis, M. A., et al, *Bio Techniques* 6:608–614 (1988) which are incorporated herein by reference]. In addition to these sequences, sequences overlapping the gag gene were found to contribute to the efficiency of viral RNA encapsidation by Moloney murine leukemia virus [Adam, M. A., et al, *J. Virol.* 62:3802–3806 (1988); Bender, M., et al., *J. Virol.* 61:1639–1646 (1987)]. Certain retroviruses have been used to introduce genetic information stably into the genome of target cells in eukaryotic cells in vivo and in vitro [Cornetta, K., *Progress in Nucleic Acids Research and Molecular Biology* 36:311–322 (1989); Gilboa, E., *Biotechniques* 4:504–512 (1986); Joyner, A., *Nature* 305:556–558 (1983); Mann, R., et al., *Cell* 33:153–159 (1983)]. Vectors containing the desired gene and packaging sequences were incorporated by packaging signal-deleted viruses generating virions capable of entry into certain cells. The signals needed for packaging of lentiviruses RNA, (such as HIV RNA) into virion particles have not been identified.

Although a great deal of research has been expended on understanding HIV-1, the life cycle of this retrovirus is not completely understood.

In addition, a great deal of research has been directed to developing a vaccine to the virus, but there have been no reports of success to date. This is, in part, due to the lack of conservation in the antigenically active parts of the virus and in part because the functionally important regions of viral proteins and/or inactivated viral particles are poorly immunogenic.

Many methods proposed for treating HIV infected individuals would adversely affect uninfected cells as well as HIV infected cells.

Accordingly, it would be extremely useful to have a provirus that produced HIV proteins but which was not lethal because the viral RNA could not be packaged into virions. Using this packaging-defective provirus vector, it would be possible to create packaging defective cell lines that could be used to investigate the packaging mechanism of the virus and to develop strategies to interfere with this packaging mechanism. Significantly, the virions produced by such packaging negative proviruses could be used for vaccines and as a system for efficiently introducing a desired gene into a mammalian cell.

It would also be useful to have a vector that could be selectively targeted to HIV target cells and could thus introduce a desired product into such cells.

SUMMARY OF THE INVENTION

We have now discovered a vector comprising a sufficient number of nucleotides corresponding to an HIV genome to express functional HIV gene products (HIV nucleotides), but which does not contain a sufficient number of nucleotides corresponding to nucleotides of the HIV genome between the 5' major splice donor and the gag gene initiation codon to efficiently package the viral RNA into virions (HIV packaging sequence). Preferably, this HIV packaging sequence corresponds to the region between the 5' major splice donor and the gag gene initiation codon (nucleotides 301–319). More preferably, this sequence corresponds to a segment just downstream of the 5' major splice donor, and about 14 bases upstream of the gag initiation codon. In one embodiment it is a 19 base segment having the sequence AAAAATTTTGACTAGCGGA.

This vector can be used to transform a preselected cell line to result in an HIV packaging defective cell line. Preferably, one would transform a cell line using at least two vectors, which collectively contain the HIV nucleotides necessary to express HIV gag, pol, and env products, but wherein each vector by itself does not contain the HIV nucleotides necessary to express all three products. In addition, each vector does not have a sufficient number of nucleotides corresponding to nucleotides of the HIV genome between the 5' major splice donor and the gag gene to efficiently package HIV RNA. More preferably, each vector would not contain a sequence corresponding to an LTR sequence downstream of the nucleotides corresponding to the HIV genes. Preferably, each vector would contain a different marker gene. The transformed cell line would express HIV virions but would not be able to package HIV RNA into these virions. Thus, these virions could be used to generate antibodies, as a vaccine or as a method of transferring a desired gene product to a different cell line capable of infection by HIV.

A second vector contains a preselected gene, a sufficient number of nucleotides corresponding to an HIV packaging sequence to package HIV RNA (HIV packaging sequence), and is flanked on each side with a sequence corresponding to a sufficient number of HIV LTR nucleotides to be packaged by the HIV packaging sequence (HIV LTR sequences), wherein the HIV packaging sequence and HIV LTR sequences correspond to the same HIV genome. This vector can be used with the packaging defective vectors to transfer the desired preselected gene. Alternatively, the vector can be administered to an HIV infected cell and be packaged by the HIV virions being produced. The HIV infected cell can be in an individual. Combinations where the HIV packaging defective vector and HIV virus as a helper virus are used together are also described. The packaging sequences are located in a region from the 5' major splice donor to a site within the 5' most part of the gag gene.

BRIEF DESCRIPTION OF THE DRAWINGS

FIG. 2a is a packaging defective vector, HXBvP1. FIG. 2b is a packaging defective vector, HXBΔP1Δenv. FIG. 2c is a packaging defective vector, pSVIIIenv 3-2. FIG. 2d is a packaging proficient vector, HVB(SL3-Neo). FIG. 2e is a packaging proficient vector, HVB(SL3-Neo).

DETAILED DESCRIPTION OF THE INVENTION

Figure 1:
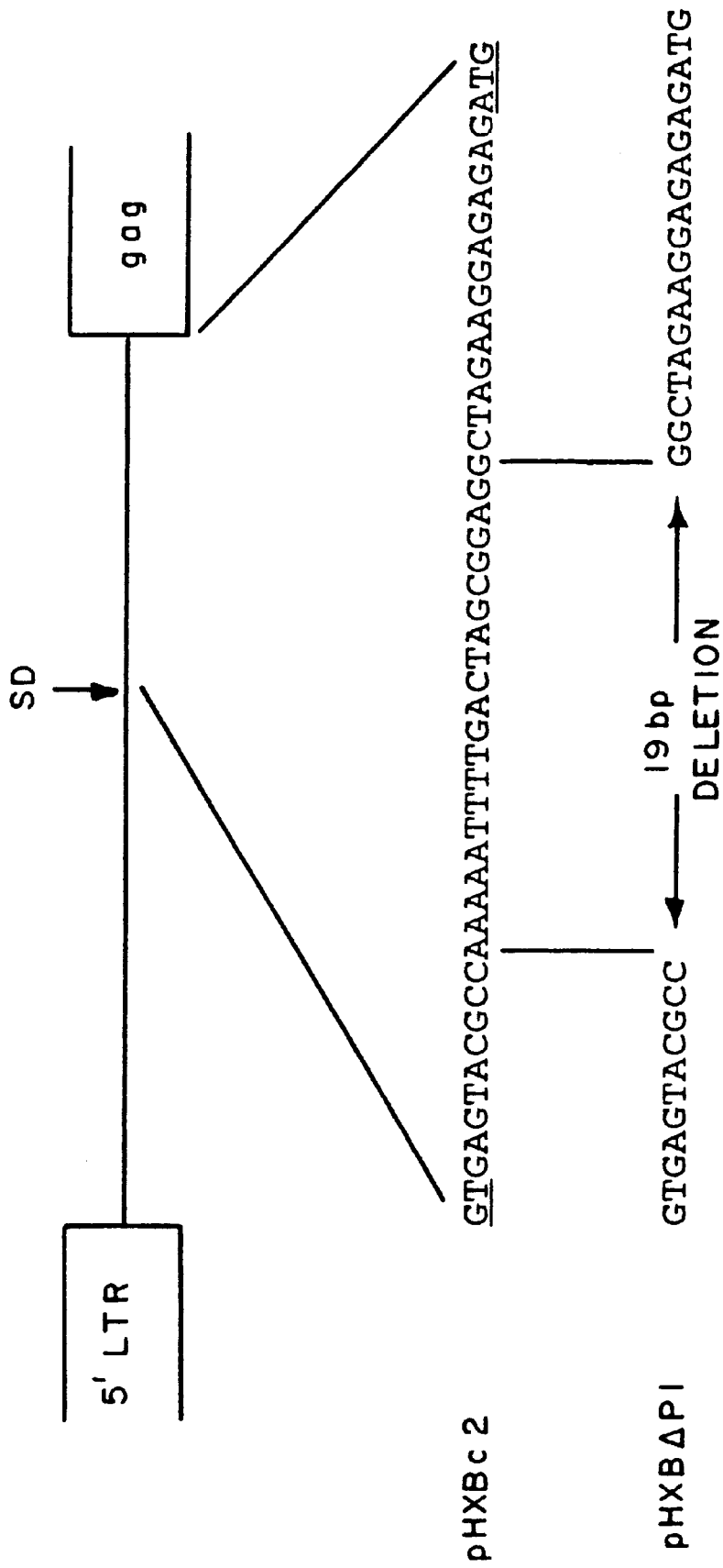
FIG. 1 is a schematic of the HIV-1 genome from the 5' LTR to the gag initiation codon showing the 5' major splice donor (SD) and the site of the deletion in a vector representing one embodiment of this invention, pHXBΔP1.

We have now discovered that it is possible to make HIV packaging defective vectors and cell lines. We have found that the region between the 5' major splice donor and the gag gene initiation codon in HIV viruses contains sequences necessary for packaging of HIV RNA into virions. One can prepare a vector comprising a packaging defective HIV provirus wherein the vector contains a nucleotide sequence which corresponds to a sufficient number of nucleotides from an HIV genome to express desired HIV products, but does not correspond to a sufficient number of nucleotides corresponding to the region between the 5' major splice donor and the gag gene initiation codon to efficiently package HIV RNA (the HIV packaging sequence).

These sequences preferably correspond to the genome of HIV-1, HIV-2 and simian immunodeficiency virus (SIV).

[See Ratner, et al, *Nature* 313, supra, Sanchez-Pescador et al, *Science* 227, supra, Muesing, et al, Nature 313, supra, Wain-Hobson et al, Cell 40, supra, Guyader, M. et al, *Nature* 326, supra (1987); Chakrabarti et al, *Nature* 328, supra (1987) and Hirsch, V., et al, *Cell* 49:307–319 (1987) which are all incorporated herein by reference].

The term corresponding means that conservative additions, deletions and substitutions are permitted.

Preferably, the vector does not contain the HIV packaging sequence corresponding to the segment immediately downstream of the 5' major splice donor and just upstream of the gag gene initiation codon. Typically, the vector could contain nucleotides ranging from about 14 bases to 2 bases upstream of the gag initiation codon (for example either the 14 upstream bases or 5 upstream bases) and still be packaging deficient. In one embodiment the vector does not contain a nucleotide sequence beginning about 9 bases downstream of the 5' major splice donor and continuing to about 14 bases upstream of the gag initiation codon. The number of bases that need to be left out can vary greatly, for example, the 19 base pair deletion AAAAATTTTGAC-TAGCGGA deletion in HIV-1 (nucleotides 301–319) is sufficient to result in loss of packaging ability (See FIG. 1). However, even smaller deletions in this region should also result in loss of packaging efficiencies. Indeed, it is expected that a deletion as small as about 5 base pairs in this region should remove packaging ability. Thus the size of a particular deletion can readily be determined based upon the present disclosure by the person of ordinary skill in the art.

The vector should contain an HIV nucleotide segment containing a sufficient number of nucleotides corresponding to nucleotides of the HIV genome to express functional HIV gene products, but as aforesaid, should not contain a sufficient number of nucleotides corresponding to the region between the 5' major splice donor and the gag gene initiation codon to permit efficient packaging of the viral RNA into virions. In using these vectors to establish HIV packaging defective cell lines it is preferred that such cell lines do not produce any infectious HIV. Although a cell line transformed by these packaging deficient vectors would have low infectivity because the cells are packaging defective, some RNA can still be packaged into the virion. Accordingly, it is preferable that the HIV nucleotide segment does not correspond to the entire HIV genome so that if some of the viral RNA is packaged into the virion, what is packaged will not be a replication competent virus.

Preferably, one would want to have at least two different vectors, each containing a different portion of the HIV genome and also not containing the sequence necessary for viral packaging. Then by co-transfecting a cell with each vector the cell would still be able to express all the HIV structural proteins and produce virions. In one preferred embodiment the vector would not contain sequences corresponding to an HIV LTR but would contain sequences corresponding to a promoter region and/or another genome's polyadenylation sequences. Selection of particular promoters and polyadenylation sequences can readily be determined based upon the particular host cell. Preferably, the LTR which the sequences do not correspond to is the 3' LTR. For example, see FIG. 3.

Figure 3:
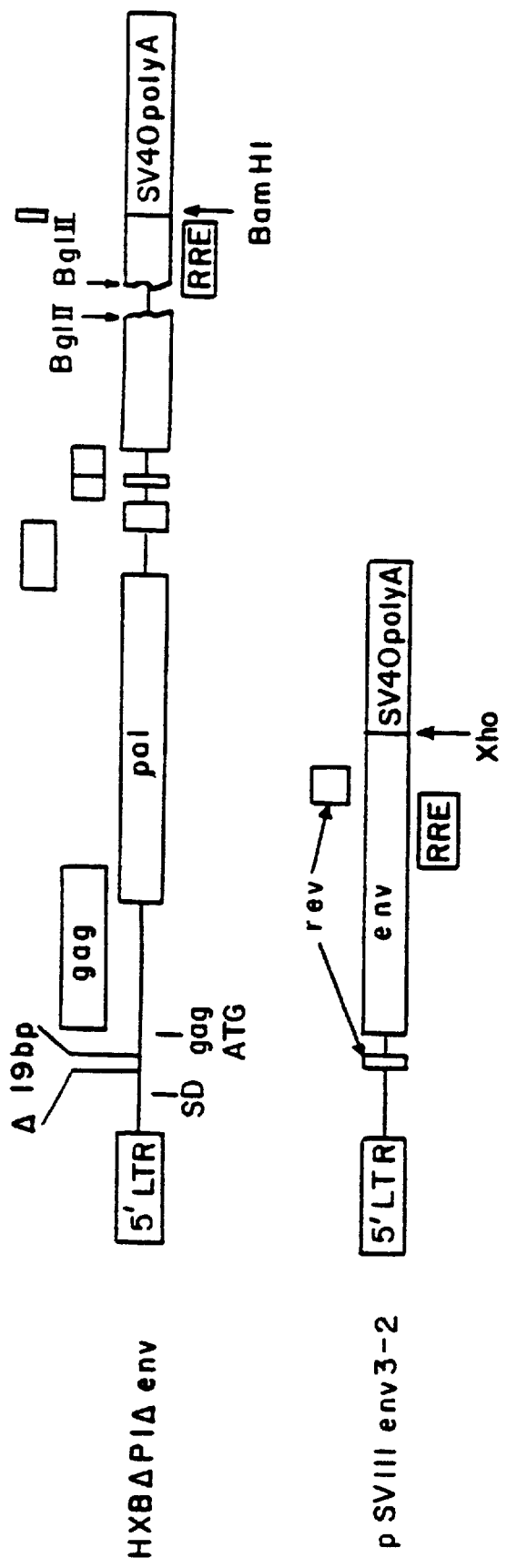
FIG. 3 is a schematic of one preferred embodiment showing two packaging deficient vectors, HXBΔP1Δenv and pSVIIIenv 3-2.

In one preferred embodiment one vector would include sequences permitting expression of HIV proteins upstream of env and the second vector would permit expression of the remaining proteins. For example, one vector would contain an HIV nucleotide segment corresponding to a sufficient number of nucleotides upstream of the gag initiation codon to the env gene sequence to express the 5'-most gene products. The other vector would contain an HIV nucleotide segment corresponding to a sufficient number of nucleotides downstream of the gag gene sequence and including a functional env gene sequence. Such vectors can be chemically synthesized from the reported sequences of the HIV genomes or derived from the many available HIV proviruses, by taking advantage of the known restriction endonuclease sites in these viruses by the skilled artisan based upon the present disclosure (FIG. 3). Preferably, one would also add a different marker gene to each vector, i.e., co-transfect a preselected cell line with these different vectors and by looking for a cell containing both markers, one would have a cell line that has been co-transfected with the two vectors. Such a cell would be able to produce all of the HIV proteins. However, although virions would be produced, the RNA corresponding to the entire viral sequences would not be packaged in these virions. One can use more than two vectors if desired, e.g. a gag-pol vector, an env vector and a vif/vpu vector.

For example, one could have a vector comprising nucleotides corresponding to a sufficient number of nucleotides of an HIV LTR at the 5' end to result in a functional LTR, (preferably it corresponds to the 5' LTR), nucleotides corresponding to the rev gene and the env gene downstream of the LTR, and at the 3' end, where the sequences do not correspond to another LTR, the sequences correspond to polyadenylation sequences, such as polyadenylation sequences corresponding to the SV40 virus (e.g., pSVIIIenv 3-2 in FIG. 3). A second vector would contain other HIV or SIV genes and contain a deletion in the packaging sequence and a deletion for the env gene. This vector would also not have a 3' LTR, but would have a polyadenylation sequence. For example, one could have a vector which would not contain a sufficient number of nucleotides corresponding to HIV packaging sequence to package HIV RNA, but would contain a nucleotide segment corresponding to a sufficient number of nucleotides corresponding to a sufficient number of nucleotides of the HIV gag and pol genes to express functional gag and pol products. Preferably, this vector would also contain a sufficient number of nucleotides corresponding to a functional tat gene. The vector would not contain a sufficient number of nucleotides to encode a functional env protein. More preferably, the vector would also contain nucleotides corresponding to other HIV regulatory genes to express functional gene products, such as vpr, vpu, vif, etc. Other combinations of vectors can also be prepared. For example, a vector that does not contain a sufficient number of nucleotides to correspond to a functional gag gene, but would have a sufficient number of nucleotides to correspond to functional pol and env genes, other vectors include one that does not contain a sufficient number of nucleotides to encode a functional pol protein, but would have a sufficient number of nucleotides to encode a different functional HIV protein, etc.

As used herein, the term a sufficient number of nucleotides permits additions, deletions and substitutions as long as the claimed functional ability is not lost. For example, if one is referring to the functional ability of packaging HIV RNA then the resultant vector must have a sequence that can package HIV RNA. =HIV-1 can be pseudotyped with the envelope glycoproteins of other viruses. [(Lusso, P., et al., *Science* 247:848–851 (1990)]. Consequently, one can prepare a vector containing a sufficient number of nucleotides to correspond to a functional env gene from a different retrovirus. Preferably, the 5' LTR of this vector would be of the same genome as the env gene. Such a vector could be used instead of an env packaging deficient vector to create virions. By such a change, the resultant vector system can be used in a wider host range.

Virtually any cell line can be used. Preferably, one would use a mammalian cell line, for example, CV-1, Hela, Raji, RD, SW480 or CHO cell lines.

In order to increase production of the viral cellular products, one could use a different promoter than the 5' LTR, i.e., replace the 5' LTR with a promoter that will preferentially express genes under its control in a particular cell line. For example, the CMV promoter will preferentially express genes in CV-1 or Hela cells. The particular promoter used can be readily determined by the person of ordinary skill in the art, based upon the particular host cell line to be used.

In order to increase the level of viral cellular products one can also add enhancer sequences to the vector to get enhancement of the HIV LTR and/or promoter. Particular enhancer sequences can readily be determined by the person of ordinary skill in the art depending upon the host cell line.

One can also add vectors that express viral enhancer proteins, such as those of herpes virus, hepatitis B virus, which act on HIV LTRs to enhance the level of virus product, or cellular transactivator proteins. Cellular transactivation proteins include NF κ-B, UV light responsive factors and other T cell activation factors well known to the person of ordinary skill in the art.

By using a series of vectors that together would contain the complete HIV genome, one can create cell lines that produce a virion that is identical to the HIV virion, except that the virion does not contain the HIV RNA. The virions can readily be obtained from these cells. For example, the cells would be cultured and supernatant collected. Depending upon the desired use the supernatant containing the virions can be used or these virions can be separated from the supernatant by standard techniques. Typically, this would include gradiant centrifugation, filtering, etc.

These attenuated virions would be extremely useful in preparing a vaccine. The virions can be used to generate an antigenic response to the HIV virions and because these virions are identical to the actual HIV virions, except that the interior of these virions do not contain the viral RNA, the vaccine created should be particularly useful.

These virions can also be used to raise antibodies to the virion that can then be used for a variety of purposes, e.g. screening for the virion, developing target system for the virions, etc.

Additionally, these HIV packaging deficient cell lines can be extremely useful as a means of introducing a desired gene, for example, a heterologous gene into mammalian cells.

These virions could be used as an extremely efficient way to package desired genetic sequences into target cells infectable by HIV. This would be done by preparing a vector containing a nucleotide segment containing a sufficient number of nucleotides corresponding to the packaging nucleotides of the HIV virus (HIV packaging region), a predetermined gene, and flanking the packaging sequence and the predetermined gene with sequences corresponding to a sufficient number of sequences from within and near the LTRs for packaging, reverse transcription, integration and gene expression. The packaging region used would preferably correspond to at least the region between the 5' major splice donor and just upstream of the gag initiation codon, more preferably the region between the 5' major splice donor and the Bal I site (2202 in HIV-1) in the gag gene.

For example, a sufficient number of HIV-1 sequences to be packaged, reverse transcribed, integrated and expressed in the target cells would inlclude the U3, R and U5 sequences of the LTRs, the packaging sequences, and some sequences flanking the LTRs (required for reverse transcription). From the 5' LTR, the R and U5 regions would be included which, in HIV-1, extend from +1 to 183. The sequences flanking the 5' LTR necessary for reverse transcription and packaging would extend from 183 to about 335. Although not wishing to be bound by theory, applicants believe the inclusion of additional sequences from the gag gene in the vector (up to the Bal I site, nucleotide 2202) should enhance packaging efficiency. The regions from the 3' LTR and the immediate flanking sequences to be included extend from about 8645 to about 9213 (U3 and R regions). Analagous regions would be included in a vector based upon HIV-2 or SIV.

When this vector is used to transfect one of the HIV packaging deficient cells, it is the nucleotide sequence from this vector that will be packaged in the virions. These "HIV packaged" genes could then be targeted to cells infectable by HIV. This method of transformation is expected to be much more efficient than current methods. Further, by appropriate choice of genes, one could also monitor the method of HIV infection.

For example, the vector could contain a sufficient number of nucleotides corresponding to both 5' and 3' LTRs of HIV-1, HIV-2 or SIV to be expressed, reverse transcribed and integrated, a sufficient number of nucleotides corresponding to an HIV packaging sequence to be packaged, for example a segment between the 5' major splice donor and just upstream of the gag initiation codon (e.g., nucleotide 381). The vector would also contain a sufficient number of nucleotides of the gene which is desired to be transferred to produce a functional gene (e.g., gene segment). The gene can be any gene desired, for example, the gene for neomycin phosphotransferase ($Neo^R$). More preferably, the "gene" would express a product that adversely affects HIV replication or integration such as a trans-dominant inhibitor, antisense RNAs, catalytic RNAs or soluble CD4 derivative. With such a gene, the vector of the present invention can be used to target HIV target cells. One would preferably include a promoter for the desired gene, although the LTR sequence, itself, can serve as a promoter. Virtually any promoter can be used. Preferably, one would use a promoter that would facilitate expression of the gene in the host cell to which the gene is to be transfered. Preferred promoters include viral promoters, such as SL-3, murine retroviral LTR, etc. Enhancers sequences are also preferably used in the vector. One would also preferably include polyadenylation sequences for the gene. One can use any polyadenylation sequence, for example, the sequences corresponding to SV-40 polyadenylation sequences. The desired gene can be inserted in the present vector, in either the sense or antisense orientation with respect to the LTRs. The vector can contain more than one gene or pseudogene sequence, permitting the expression of multiple genes of interest.

This vector can preferably be used with the packaging-defective vectors described above. In such a situation, one preferably uses HIV LTRs in the vector corresponding to the genome of the package-deficient vector to facilitate packaging efficiency. However, in addition to use with a packaging-deficient virus, this vector can also be used with helper virus for gene transfer. For example, when one wants to deliver a gene to treat an individual infected with AIDS, one could insert this vector into that individual and it would be incorporated into HIV virions being produced in that individual. This would facilitate the delivery of the desired gene to the appropriate target cell. Accordingly, one could use this to deliver trans-dominant inhibitors, anti-sense RNAs, catalytic RNAs, or soluble CD4 derivatives which are also aimed at inhibiting HIV-1 functions critical for viral replication. One could also deliver this material by using the packaging-defective vectors described herein or such packaging defective vectors in combination with the HIV virus in an infected individual.

Additionally, these HIV packaging defective cell lines can be used to study various stages of the HIV life cycle, both in vivo and in vitro systems by a system because the cells will express HIV cellular proteins, but will not package the RNA.

The present invention is further illustrated by the following examples. These examples are provided to aid in the understanding of the invention and are not to be construed as limitation thereof.

The region between the HIV-1 5' LTR and the gag gene is shown in FIG. 1 which shows the 5' major splice donor (SD) and site of deletion in a vector described below, pHXBΔP1. A 19 base-pair deletion in this region was created in an infectious HIV-1 proviral clone contained on the plasmid pHXBc2 of Fisher, A. G., et al, Nature 316: 262–265 (1985). This plasmid also contains an SV40 origin of replication to allow efficient gene expression in COS-1 cells. The mutation was produced by the site-directed mutagenesis as described in Kunkel, T. A., et al, Methods in Enzymology 154, 367–382 (1987), and the sequence confirmed by DNA sequencing (Sanger, F., et al, Proc. Natl. Acad. Sci. 74:5463–5467 (1977). The mutated plasmid was designated pHXBvP1.

Figure 2:
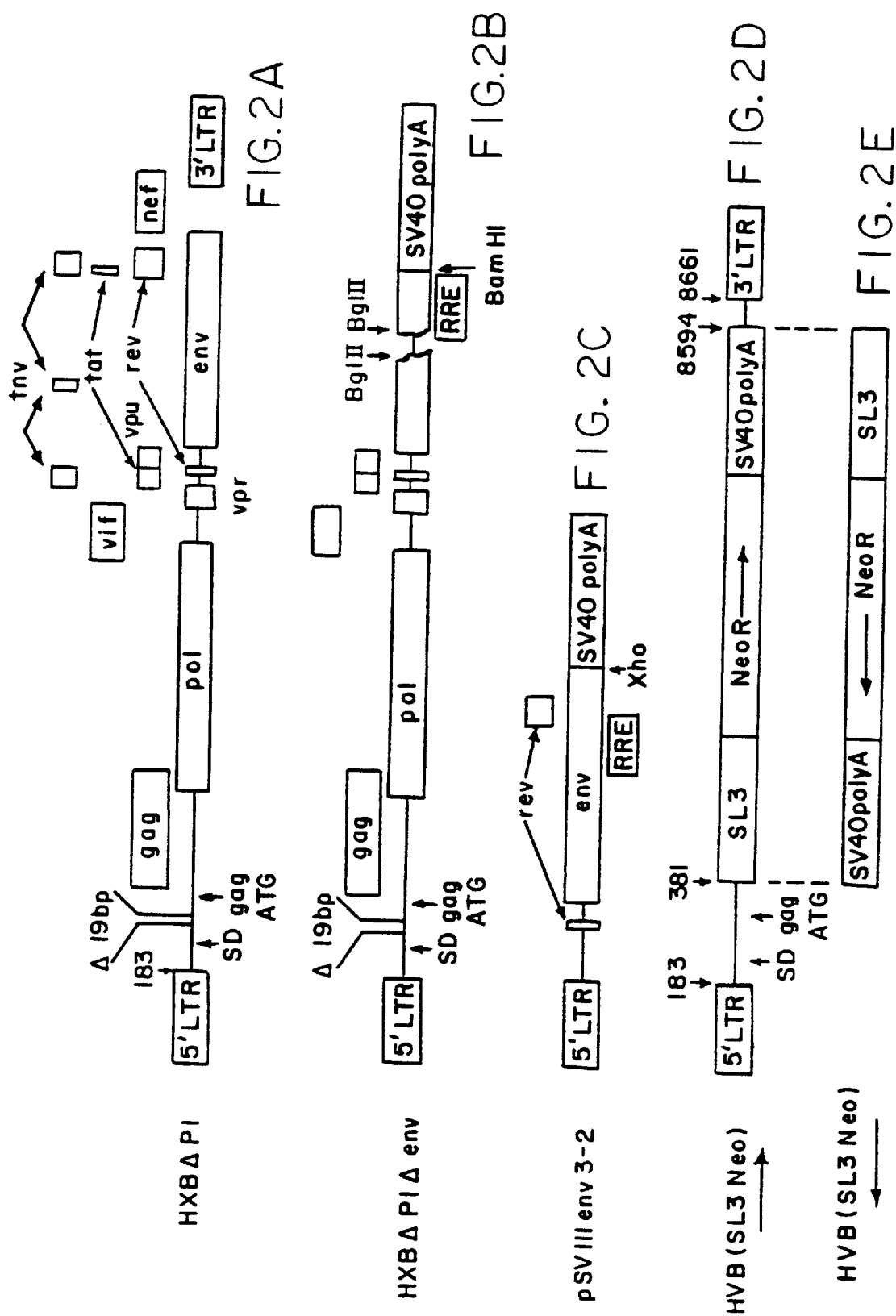
FIGS. 2a–e represents schematics of vectors representing various embodiments according to this invention.

An additional out-of-frame deletion between the Bgl II sites (nucleotides 6620 to 7199) was created in the env gene. See FIG. 2b. Then, polyadenylation signals from SV40 were substituted for the 3' end of the pHXBΔP1 provirus beginning at the BamHI site (nucleotide 8053) to prepare HXBΔP1Δenv. The pSVIIIenv3-2 plasmid encodes the HIV-1 env and env genes, with polyadenylation signals derived from SV40. In the pSVIIIenv 3-2 plasmid, the rev and env genes of HIV-1 are under the control of the HIV-1 LTR. The construction of this vector has been previously described. (See Sodroski, et al., Nature 321:412–417 (1986) and Sodroski, et al., Nature 322:470–474 (1986), which are incorporated herein by reference. The maps of the relevant portions of the plasmids used are shown in FIG. 2. For the HXBΔP1 and HXBΔP1Δenv vectors, the positions of the HIV-1 genes are shown along with the location of a nineteen base pair deletion previously described (Δ19 bp). And for HXBΔP1Δenv and pSVIIIenv 3-2, the rev responsive element (RRE), and the SV40 polyadenylation signal (SV40 polyA) are shown.

COS-1 cells were maintained in Dulbecco's modified Eagle's medium DMEM (Hazelton Biologics, Lenexa) supplemented with 10% fetal calf serum (Gibco, Long Island, N.Y.) and antibiotics. Jurkat cells were maintained in culture in RPMI 1640 with 10% fetal calf serum and antibiotics. Jurkat cells were preventatively treated for mycoplasma with B. M. Cyclin I and II and human serum two weeks prior to infection. The HXBc2 (gag$^+$, pro$^+$, pol$^+$, vif$^+$, vpr$^-$, vpu$^-$, tat$^+$, rev$^+$, env$^+$, nef$^-$) provirus was used in all plasmids was used in all plasmid and vector constructs.

Figure 5A:
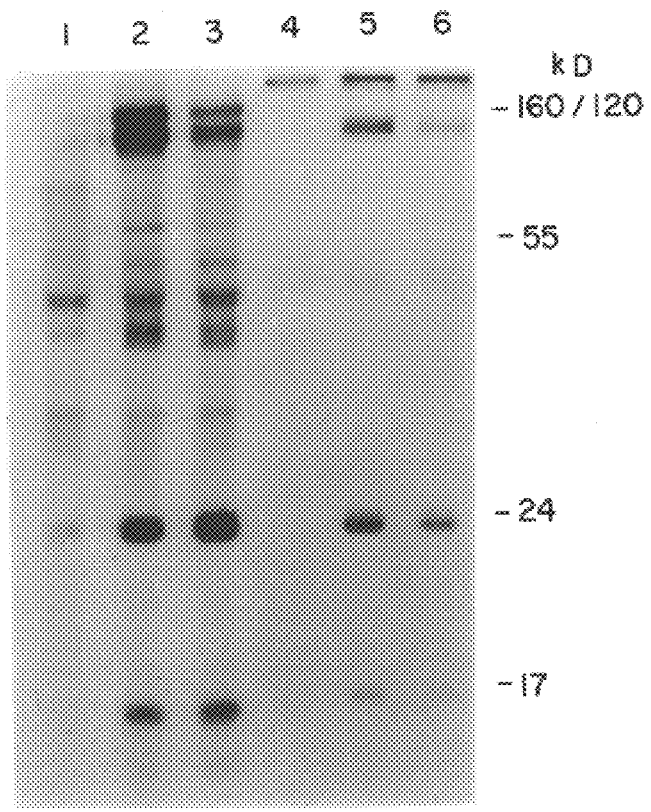
FIG. 5a is an autoradiogram of the immunoprecipitation of $^{35}$S-labelled viral protein from COS-1 cells transfected with pHXBΔP1 DNA with AIDS patient serum.
Figure 5B:
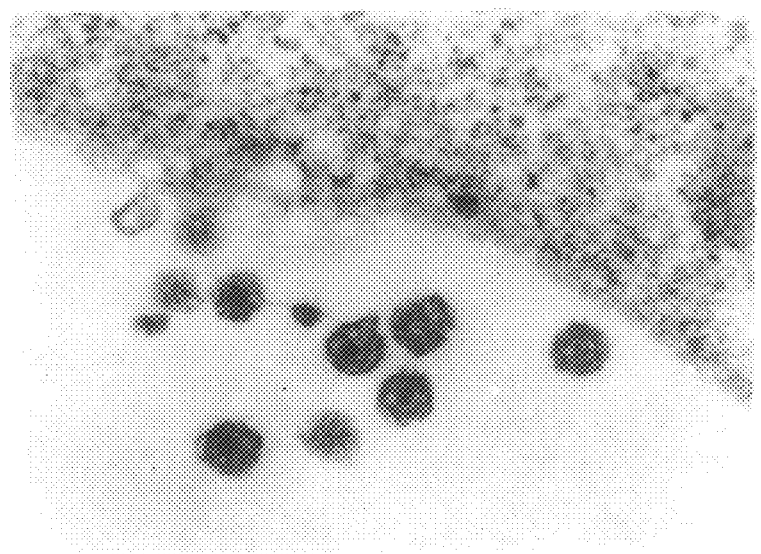
FIG. 5b is an electron micrograph of COS-1 cells transfected with pHXBΔP1 showing virion particles of normal HIV-1 morphology.

To evaluate the effect of the mutation on viral protein expression and virion production, COS-1 cells were transfected with the pHXBc2 and pHXBΔP1 plasmids by the DEAE-dextran procedure [Lopata et al, Nucl. Acids Res. 12:5707–5717 (1984); Queen and Baltimore, Cell 33:741–748 (1983); (Sodroski, J., et al, Science 231:1549–1553 (1986) which are incorporated herein by reference]. COS-1 cell lysates and supernatants radiolabelled with $^{35}$S-cysteine (Sodroski, J., et al, Science 231, supra) at 48 hours after transfection were precipitated with 19501 AIDS patient serum. The overall level of viral protein detected in cell lysates was comparable for the vectors containing the wild-type HXBc2 and the HIV packaging defective HXBΔP1. See FIG. 5A, which shows immunoprecipitation of $^{35}$S-labelled viral proteins from COS-1 cell lysates (lanes 1–3) or supernatants (lanes 4–6) with 19501 patient serum, after transfection with no DNA (lanes 1 and 4), 10 μg pHXBc2 (lanes 2 and 5) or 10 μg pHXBΔP1 (lanes 3 and 6). The overall level of viral protein detected in cell lysates was comparable for cells transfected by either HXBc2 or HXBΔP1. The level of viral proteins precipitated from the supernatants of COS-1 cells was slightly less with HXBΔP1 than with HXBc2. The amount of reverse transcriptase (RT) activity measured in the supernatants of COS-1 cell transfected by pHXBΔP1 was 60% of that measured in cells transfected with the HXBc2 vector (data not shown). COS-1 cells transfected with pHXBΔP1 were fixed 48 hours following transfection and examined by electron microscopy. Viral particles, including budding forms, of normal HIV-1 morphology were observed. FIG. 5B is an electron micrographs of COS-1 cells transfected with PHXBΔP1 showing virus particles of normal HIV-1 morphology.

Figure 6:
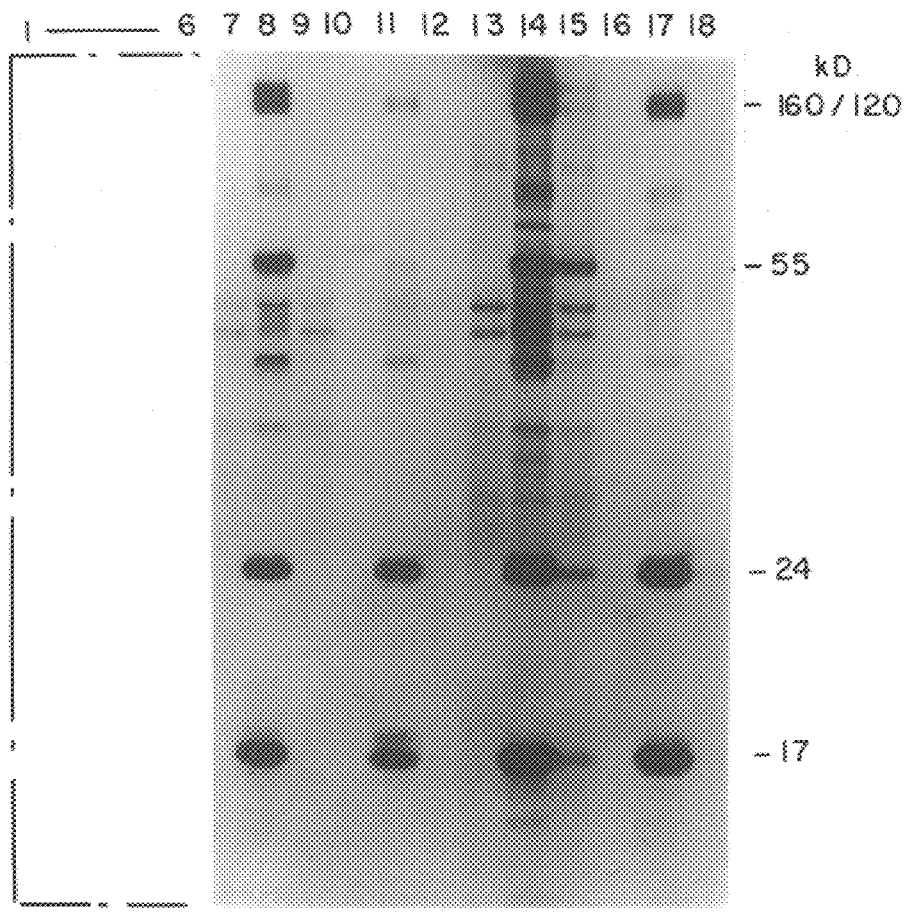
FIG. 6 is an autoradiogram of immunoprecipitation of labelled viral proteins from Jurkat T cell lysates or supernatants exposed to supernatants from COS-1 cells that were transfected or mock transfected.

To evaluate the effect of the HXBΔP1 mutation on HIV-1 replication, supernatants from COS-1 cells transfected with pHXBc2 and pHXBΔP1 were filtered (0.2μ) and RT measured. Supernatants containing equal amounts of RT activity of mutant and wild-type viruses were added to Jurkat human T lymphocytes. The Jurkat cultures along with a mock-infected culture were maintained with medium changes every three days. At intervals aliquots of Jurkat cells were labelled and assessed for expression of HIV-1 proteins by immunoprecipitation with 19501 AIDS patient serum. FIG. 6 shows immunoprecipitation of labelled viral proteins from Jurkat T cell lysates (lanes 1–3, 7–9 and 13–15) or supernatants (lanes 4–6, 10–12 and 16–18) exposed to supernatants from COS-1 cells that were mock transfected (lanes 1, 4, 7, 10, 13 and 16), pHXBc2 (lanes 2, 5, 8, 11, 14 and 17), or transfected with pHXBΔP1 (lanes 3, 6, 9, 12, 15 and 18). The Jurkat cells were examined at day 7 (lanes 1–6), day 14 (lanes 7–12) and day 21 (13–18) following infection. Jurkat cultures exposed to HXBΔP1 exhibited marked delays in and lower levels of viral protein production relative to those exposed to pHXBc2, the wild-type virus. Virus replication in human T lymphocytes transfected by HXBΔP1 is thus seen to be significantly attenuated compared with cells transfected by HXBc2.

Figure 7:
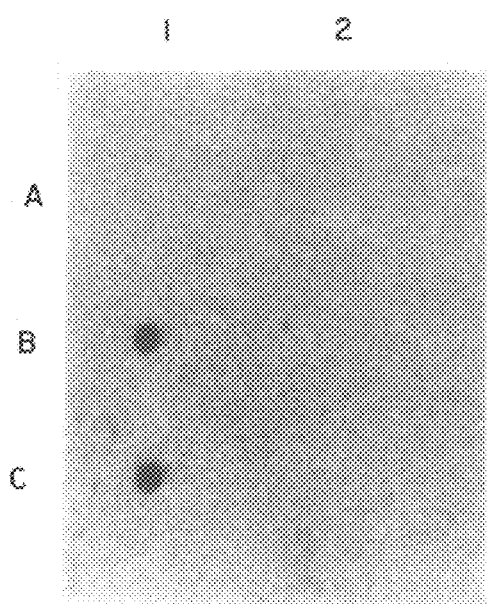
FIG. 7 is an RNA dot blot test.

Supernatants from the above cultures were 0.2μ-filtered and equivalent amounts of reverse transcriptase activity pelleted by centrifugation at 12000 xg for one hour at 20° C. Viral pellets were lysed by NP40 in the presence of vanadyl ribonucleotides and dilutions of virus dot-blotted onto nitrocellulose filters. Some samples were treated with sodium hydroxide (5M at 60° C. for 15 minutes) prior to dot-blotting. Filters were hybridized with a DNA probe consisting of HIV-1 gag and env gene sequences, washed and autoradiographed as previously described in Maniatis, T., et al, Molecular Cloning, Cold Spring Harbor Laboratory, (1982). For the wild-type HXBc2 virus, a signal specific for RNA could be detected after blotting 1000 reverse transcriptase units of filtered supernatant (not shown). For the HXBΔP1, even 5×10$^4$ reverse transcriptase units of supernatant gave no detectable signal. FIG. 7 is an RNA dot blot without (column 1) and with (column 2) sodium hydroxide treatment following blotting of filtered supernatants from the Jurkat cultures. The supernatants contained a reverse transcriptase activity of $5 \times 10^4$ cpm of HXBΔP1 (row A), $5 \times 10^4$ cpm of HXBc2 (row B), or $1 \times 10^5$ cpm of HXBc2 (row C). These results indicate that the efficiency of packaging virus-specific RNA into virions for cells transfected with a packaging defective viral vector according to the present invention is less than 2% of the wild-type virus.

The results indicate that the region between the 5' LTR and gag gene of HIV-1 is important for packaging viral RNA into virions. A mutation in this region exhibits minimal effects on the ability of the provirus to produce proteins and virion particles following transfection, but markedly decreases the level of virion RNA and attenuates virus replication in a human CD4-positive lymphocyte line. HIV-1 replicates in cultured CD4-positive cells via cell-free transmission and cell-to-cell transmission, the latter involving the contact of infected and uninfected cells [Fisher, A. G., et al, *Nature* 316:262–265 (1985), Sodroski, J., et al, *Science* 231:1549–1553 (1986), Strebel, K., et al, *Nature* 328:728–730 (1987)].

Vectors based on HIV-1 packaging sequences were constructed.

The pHVB(SL3-Neo)sense (pHVB (SL3-Neo))

and pHVB (SL3-Neo)anti-sense (PHVB (SL3-Neo))

plasmids contain the coding sequence of the neo gene under the control of the SL3-3 murine leukemia virus LTR, with polyadenylation signals derived from SV40. The pHVB (SL3-Neo)sense and pHVB(SL3-Neo) anti-sense plasmids contain complete 5' and 3' HIV-1 LTRs and flanking viral sequences nucleotides 183–381 near the 5' LTR and nucleotides 8504–8661 adjacent to the 3' LTR. A unique Bam HI site was inserted at the boundaries of the major deletion in the HXBc2 provirus (nucleotides 382 to 8593), and the SL3 LTR-Neo transcription unit was cloned into this site in either the sense (pHVB (SL3-Neo))

or antisense (pHVB (SL3-Neo))

orientation with respect to the HIV-1 LTRs. All of the plasmids contained SV40 origins of replication. See FIG. 2. These vectors include the 19 base pair sequence shown by deletion to be important for packaging viral RNA. The vectors cannot encode any of the HIV-1 gene products. The vectors contain an insert in which the SL3-3 murine retroviral LTR, which functions as an efficient promoter in T lymphocytes, promotes the expression of the neomycin phosphotransferase (Neo$^R$) gene. The polyadenylation signals for the Neo transcript are provided by sequences from SV40. Numbers above the plasmid in FIG. 2 indicate the nucleotide of the HXBc2 sequence that form the boundaries of provirus/insert. The SL3-3 murine leukemia virus LTR is indicated SL3. The position of the major 5' splice donor (SD) and gag gene initiation codon (gagATG) are shown in the figure.

50% confluent COS-1 cells were transfected with plasmid DNA for the systems HXBΔP1+HVB (SL3-Neo)sense; HXBΔP1+HVB(SL3-Neo)anti-sense, HVB(SL3-Neo)sense +pHXBΔP1Δenv +pSVIIIenv 3-2; and HVB(SL3-Neo)anti-sense+pHXBΔP1Δenv +pSVIIIenv 3-2 using 10 μg/ml of each plasmid by the calcium phosphate method [Chen, C., et al., *Mol. Cell. Biol.* 7:2745–2752 (1987)] to generate recombinant viruses. DMEM containing FCS and antibiotics was placed in COS-1 cell cultures 12 hours after transfection. COS-1 supernatants were harvested and filtered through a 0.2 μm filter (Millipore) 72 hours post transfection. The p24 level in the COS-1 supernatants was determined by a p24 radioimmunoassay (Dupont).

Jurkat cells to be infected with virus were seeded into 6-well culture plates at a $2.5 \times 10^5$ cells per well in 2.5 ml of complete medium. Ten-fold serial dilutions of transfected COS-1 supernatants were then applied to each well and the virus allowed to absorb to the Jurkat cells at 37° C. for 4 hours. After this the Jurkat cells were pelleted and resuspended in complete medium. Twenty-four hours later the medium was replaced by complete medium containing G418 (Gibco, N.Y.) at an active concentration of 0.8 mg/ml and the cells dispensed into 24-well culture plates at $1.0 \times 10^4$ cells per well. Culture medium was changed every 4 days. Positive wells containing clusters of viable G418-resistant cells were identified and counted in cultures 18 days post-infection. Levels of p24 in infected Jurkat cell culture medium were determined at 5, 10, and 20 days post-infection by radioimmunoassay. The level of syncytium formation by infected Jurkat cells was also determined in cultures 5 to 20 days post-infection.

To clone the G418-resistant Jurkat cells, the cells were washed in phosphate-buffered saline and diluted to a concentration of 0.5 viable cells per 100 μl medium. Then 100 μl of the cell suspension was dispensed into each well of a 96-well culture plate. Wells containing single cells were identified by phase contract microscopy and individual cells were expanded to $10^7$ cells in complete medium containing 0.8 mg/ml G418.

Genomic DNA was prepared from clones, digested with SacI and Southern blotted as previously described by Southern, E. M, *J. Mol. Biol.* 98:503–517 (1975). Southern blots were hybridized to a 3.3 Kb fragment containing the SL3 LTR, neo gene and SV40 polyadenylation sequences that had been labelled by random priming with oligonucleotides. Southern blots were washed under conditions of high stringency.

The pHXBΔP1 plasmid and the HIV-1 vectors were cotransfected into COS-1 cells as described above. Table 1 shows that gag p24 protein of HIV-1 was detectable in the supernatant of these transfected cells on the third day after transfection. The filtered COS-1 supernatants were serially diluted and incubated with Jurkat lymphocytes, which were selected for G418-resistance. The number of G418-resistant Jurkat cells generated (Table 1) ranged from $10^2$ to $10^5$ per milliliter of COS-1 supernatant, with the HVB(SL3-Neo) anti-sense vector yielding higher titers than the HVB(SL3-Neo)sense vector. No G418-resistant Jurkat cells were generated following incubation with supernatant derived from COS-1 cells transfected with no DNA, the vectors alone, or the pHXBΔP1 plasmid alone.

Figure 4:
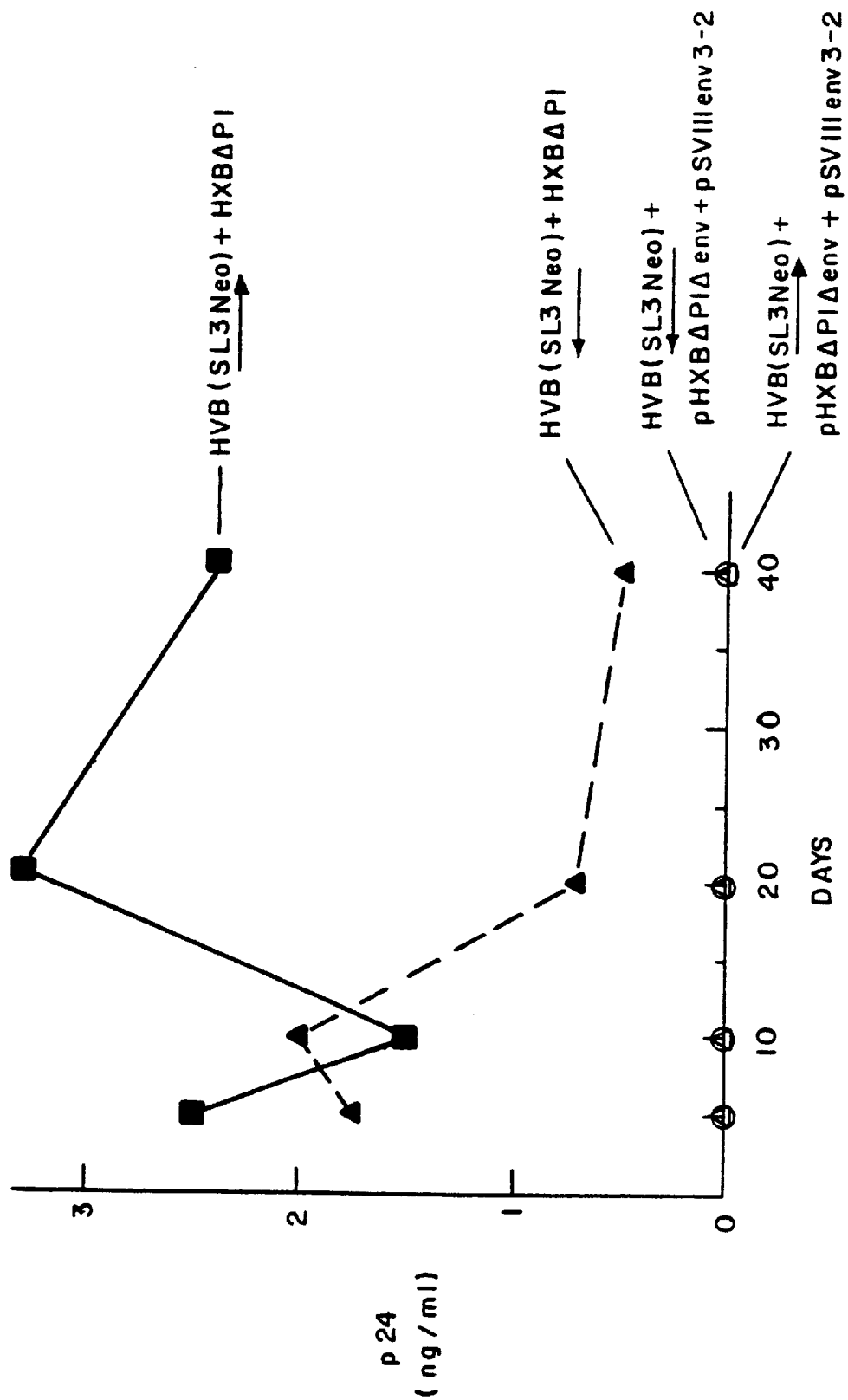
FIG. 4 is a chart showing p24 Levels in Culture of Infected Jurkat Cells by vectors representing various embodiments of this invention.

The HXBΔP1 provirus is not completely replication defective. Thus, the production of viral p24 antigen and the formation of syncytia were examined to determine the amount of infectious virus in the G418-resistant Jurkat cells. FIG. 4 shows that HIV-1 p24 antigen was detectable in the supernatants of the Jurkat cultures. Syncytium formation was visible and increased with time in these cultures, indicating the expression of the HIV-1 envelope glycoproteins in the target cells. The induction of significant cytophathic effect in these cultures made cloning of the G418-resistant Jurkat cells difficult, and further suggested the presence of replication-competent viruses in the target cells. See also Table 2.

TABLE 1

Viral p24 Antigen Expression And Recombinant Viral Titers In Supernatants of Transfected COS-1 Cells.

| Transfected DNA | p24(ng/ml)[a] | G418-resistant titers cfu/ml)[a] |
|---|---|---|
| None | 0 | 0 |
| pHVB(SL3-Neo)sense | 0 | 0 |
| pHVB(SL3-Neo)anti-sense | 0 | 0 |
| pHXBΔP1 | 0.6 | 0 |
| pHXBΔP1 + pHVB(SL3-Neo)sense | 6.1 | $5 \times 10^2$ |
| pHXBΔP1 + pHVB(SL3-Neo)anti-sense | 22.0 | $1 \times 10^4$ |
| None | 0 | 0 |
| pSVIIIenv3-2 | 0 | 0 |
| pHXBΔP1Δenv | 5.6 | 0 |
| pHXBΔP1Δenv + pSVIIIenv3-2 + pHVB(SL3-Neo))sense | 2.5 | $1 \times 10^5$ |
| pHXBΔP1Δenv + pSVIIIenv3-2 + pHVB(SL3-Neo)anti-sense | 1.1 | $1 \times 10^4$ |

[a]Values shown are the mean results of three experiments.

Two other plasmids described above encoding the HIV-1 proteins were utilized instead of the HXBΔP1 provirus. The pHXBΔP1Δenv plasmid is identical to the pHXBΔP1 plasmid except that the provirus in the former contains a deletion in the env gene and contains a polyadenylation signal from SV40 in place of the 3' LTR. The pSVIIIenv3-2 plasmid encodes both rev and env genes of HIV-1 under the control of the HIV-1 LTR, with polyadenylation signals derived from SV40. When these two plasmids were cotransfected into COS-1 cells along with the pHVB(SL3-Neo) sense or pHVB(SL3-Neo) anti-sense plasmids by the methods described above, p24 gag antigen could be detected in the supernatants three days after transfection (Table 1). Incubation of these supernatants with Jurkat lymphocytes and selection of the Jurkat cells with G418 indicated that the level of recombinant virus ranged form $10^4$ to $10^6$ colony-forming units per milliliter of filtered supernatant. In these experiments, no significant differences were noted between experiments, and no significant difference was noted between the HVB(SL3-Neo)sense and HVB(SL3-Neo)anti-sense vectors in three separate experiments.

Figure 8A:
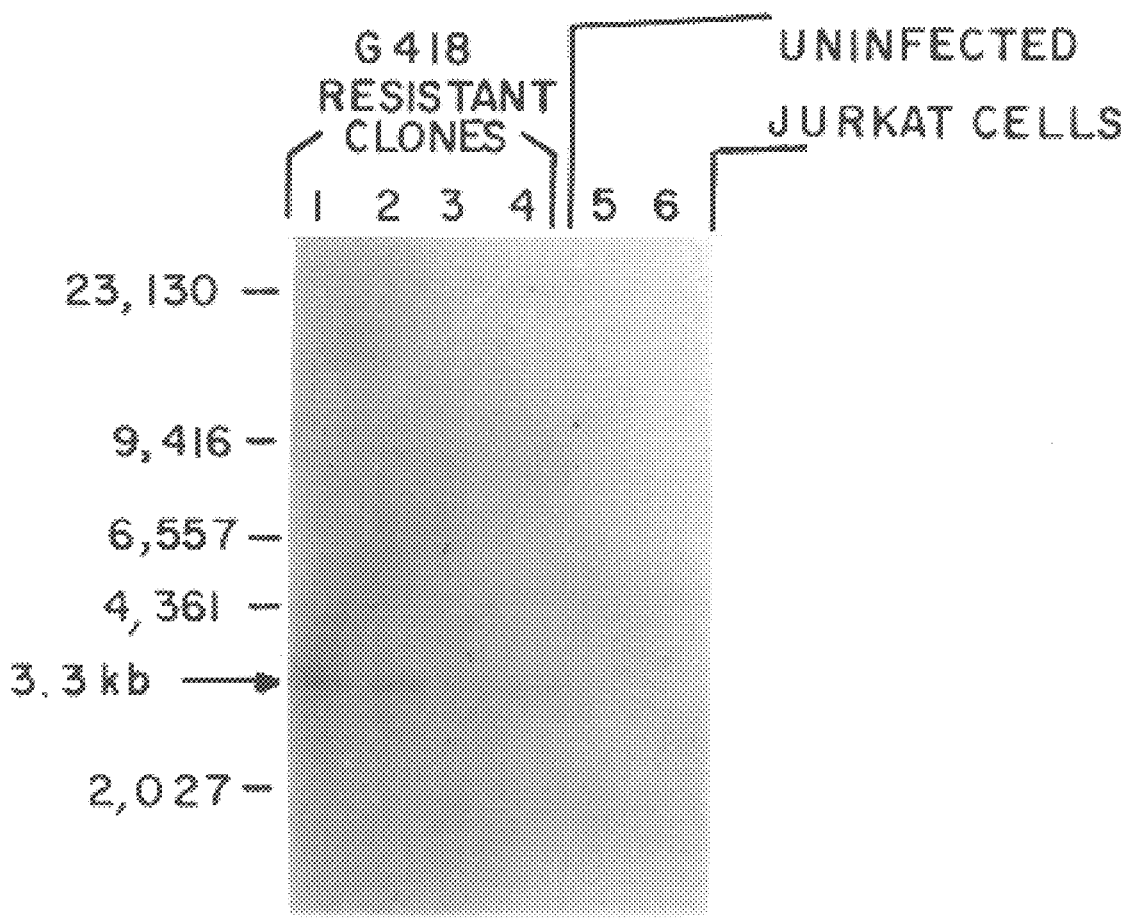
FIG. 8 is an autoradiogram showing the Sourthern blot of total DNA of G418-resistant Jurkat cells.

These G418-resistant Jurkat cells were cloned and used for isolation of DNA. The genomic DNA was digested with SacI, which cuts the vectors once in each of the HIV-1 LTRs to produce a 3.3 Kb fragment. A fragment which contains sequences derived from the SL3-3 LTR, the coding sequences of the Neo[R] gene, and SV40 polyadenylation signals was used as a probe. Clones derived from both the HVB(SL3-Neo)sense and HVB(SL3-Neo)anti-sense vectors demonstrated a single hybridizing band at 3.3 Kb that was not seen in control Jurkat cells. See FIG. 8. This demonstrates that the HVB(SL3-Neo)sense and HVB(SL3-Neo) anti-sense sequences had been transferred without rearrangement or recombination into the G418-resistant Jurkat cells.

p24 gag protein was measured in cell supernatants and syncytia were scored up to 40 days following the initial infection. In all of the clones examined, no syncytia were observed and p24 antigen was undetectable. See Table 2. This indicates that no replication-competent virus was present in these G418-resistant Jurkat cells.

TABLE 2

Syncytium Formation in G418-resistant Jurkat Cultures[a]

| DNA Transfected into COS-1 Cells | Days After Infection | | | |
|---|---|---|---|---|
| | 5 | 10 | 20 | 40 |
| pHXBΔP1 + pHVB(SL3-Neo)sense | − | + | +++ | ND |
| pHXBΔP1 + PHVB(SL3-Neo)anti-sense | − | − | ++ | ND |
| pHXBΔP1Δenv + pSVIIIenv3-2 + pHVB(SL3-Neo)sense | − | − | − | − |
| pHXBΔP1Δenv + pSVIIIenv3-2 + pHVB(SL3-Neo)anti-sense | − | − | − | − |

[a]Syncytia were scored according to the following criteria: −, no syncytia observed; +, 1–5 syncytia/hpf; ++, 5–10 syncytia/hpf; +++, greater than 10 syncytia/hpf (hpf = high power field).

The results suggest that the packaging-defective HXBΔP1 provirus can provide trans-acting viral functions required for the transfer of a HIV-1 vector to Jurkat lymphocytes. The HIV-1 LTRs and the immediate flanking sequences, including the sequences defined to be important for packaging viral RNA, appear to be sufficient to allow packaging, reverse transcription and integration. By providing the trans-acting functions on two separate plasmids, each lacking a 3' LTR, the transfer of vector sequences occurs in the apparent absence of replication-competent virus. The titers of recombinant virus in this helper virus-free context appear to be improved relative to those observed in the presence of replication-competent virus, probably because of the induction of significant cytopathic effects by the latter. The higher titer observed for the HVB(SL3-Neo)anti-sense vector relative to the HVB(SL3-Neo)sense vector in the presence of replication-competent virus may in part relate to a suppressive effect of anti-sense read-through transcripts from the SL3 promoter on helper virus replication.

The HIV-1 vector described herein provides a simple, efficient means of introducing individual genes of interest into potential HIV-1 target cells. In light of recent observations demonstrating that HIV-1 can be pseudotyped with the envelope glycoproteins of other viruses, increasing the host range of these vectors is feasible. Given the ability of the wild-type HIV-1 genome to encode multiple gene products, these vectors are readily adaptable for the expression of multiple genes of interest in the target cells.

It is evident that those skilled in the art, given the benefit of the foregoing disclosure, may make numerous modifications thereof and departures from the specific embodiments described herein, without departing from the inventive concepts and the present invention is to be limited solely by the scope and spirit of the appended claims.

We claim:

1. At least two vectors, wherein there is at least a first vector and a second vector, said vectors comprising:
 (a) a first HIV vector, containing nucleotides sufficient to encode an HIV gag protein, wherein said nucleotides are operably linked to a promoter and a polyadenylation sequence;

(b) a second vector, nucleotides sufficient to encode a functional env gene of a virus other than HIV, wherein said nucleotides are operably linked to a promoter and a polyadenylation sequence;

wherein the vectors, when ex-pressed in combination, form a pseudotyped virion containing an envelope protein other than the HIV env protein around an HIE capsid; and wherein said vectors do not contain a sufficient number of nucleotides to encode the HIV gag, env and pol proteins on a single vector; and wherein said vectors do not contain nucleotides of the HIV genome, referred to as the HIV packaging segment, between the 5' major splice donor and the gag gene sufficient to effectively package HIV RNA; and wherein said vectors, when expressed in combination, do not form a replication competent virus.

2. The at least two vectors of claim 1, wherein said vectors, when expressed in combination, express an HIV pol protein.

3. The at least two vectors of claim 2, wherein nucleotides sufficient to encode said HIV pol protein are on said first vector.

4. At least three vectors, wherein there is at least a first, second and third vector, said vectors comprising:

(a) a first vector, containing nucleotides sufficient to encode an HIV gag protein, operably linked to a promoter and a polyadenylation sequence;

(b) a second vector, containing nucleotides sufficient to encode a functional env gene of a virus other than HIV, operably linked to a promoter and a polyadenylation sequence; and (c) a third vector containing a gene or interest, operably linked to a promoter and an HIV packing sequence necessary to package HIV RNA into HIV virions;

wherein the first and second vector, when expressed in combination, form a pseudotyped virion containing an envelope protein other than the HIV env protein around an HIV capsid; and wherein said vectors do not contain a sufficient number of nucleotides to encode the HIV gag, env and pol proteins on a single vector; and wherein said first and second vectors do not contain nucleotides of the HIV genome, referred to as the HIV packaging segment, between the 5' major splice donor and the gag gene sufficient to effectively package HIV RNA; and wherein said vectors, when expressed in combination, do not form a replication competent virus.

5. The at least three vectors of claim 4, wherein said first and second vector, when expressed in combination express an HIV pol protein.

6. The at least three vectors of claim 5, wherein nucleotides sufficient to encode said HIV pol protein are on said first vector.

7. At least two vectors, wherein there is at least a first vector and a second vector, said vectors comprising:

(a) a first HIV vector, containing nucleotides sufficient to encode an HIV gag protein, wherein said nucleotides are operably linked to a promoter and a polyadenylation sequence;

(b) a second vector, nucleotides sufficient to encode a functional env gene of a virus other than HIV, wherein said nucleotides are operably linked to a promoter and a polyadenylation sequence;

wherein the vectors, when expressed in combination, form a pseudotyped virion containing an envelope protein other than the HIV env protein around an HIV capsid;

(c) wherein said first or said second vector contains nucleotides sufficient to encode an HIV pol protein, wherein said nucleotides are operably linked to a promoter and a polyadenylation sequence; and wherein said vectors do not contain a sufficient number of nucleotides to encode the HIV gag, env and pol proteins on a single vector; and wherein said vectors do not contain nucleotides of the HIV genome, referred to as the HIV packaging segment, between the 5' major splice donor and the gag gene sufficient to effectively package HIV RNA; and wherein said vectors, when expressed in combination, do not form a replication competent virus.

8. At least three vectors, wherein there is at least a first vector, a second vector, and a third vector, said vectors comprising:

(a) a first HIV vector, containing nucleotides sufficient to encode an HIV gag protein, operably linked to a promoter and a polyadenylation sequence;

(b) a second vector containing nucleotides sufficient to encode a functional env gene of a virus other than HIV, operably linked to a promoter and a polyadenylation sequence;

(c) a third vector, containing nucleotides sufficient to encode an HIV pol protein, operably linked to a promoter and to a polyadenylation sequence;

wherein the vectors, when expressed in combination, form a pseudotyped virion containing an envelope protein other than the HIV env protein around an HIV capsid;

wherein said vectors do not contain a sufficient number of nucleotides to encode the HIV gag, env and pol proteins on a single vector; and wherein said vectors do not contain nucleotides of the HIV genome, referred to as the HIV packaging segment, between the 5' major splice donor and the gag gene sufficient to effectively package HIV RNA; and wherein said vectors, when expressed in combination, do not form a replication competent virus.

9. At least three vectors, wherein there is at least a first, second and third vector, said vectors comprising:

(a) a first vector, containing nucleotides sufficient to encode an HIV gag protein, operably linked to a promoter and a polyadenylation sequence;

(b) a second vector, containing nucleotides sufficient to encode a functional env gene of a virus other than HIV, operably linked to a promoter and a polyadenylation sequence; and (c) a third vector contains a gene or interest, operably linked to a promoter and an HIV packing sequence necessary to package HIV RNA into HIV virions;

(d) and wherein said first or second vectors contain nucleotides sufficient to encode an HIV pol protein, wherein said nucleotides are operably linked to a promoter and a polyadenylation sequence;

wherein the first and second vector, when expressed in combination, form a pseudotyped virion containing an envelope protein other than the HIV env protein around an HIV capsid; and wherein said vectors do not contain a sufficient number of nucleotides to encode the HIV gag, env and pol proteins on a single vector; and wherein said first and second vectors do not contain nucleotides of the HIV genome, referred to as the HIV packaging segment, between the 5' major splice donor and the gag gene sufficient to effectively package HIV RNA; and wherein said vectors, when expressed in combination, do not form a replication competent virus.

10. At least four vectors, wherein there is at least a first, second, third, and fourth vector, said vectors comprising:

(a) a first vector containing nucleotides sufficient to encode an HIV gag protein, wherein said nucleotides are operably linked to a promoter and a polyadenylation sequence;

(b) a second vector containing nucleotides sufficient to encode a functional env gene of a virus other than HIV, wherein said nucleotides are operably linked to a promoter and a polyadenylation sequence; and (c) a third vector containing nucleotides sufficient to encode an HIV pol protein, wherein said nucleotides are operably linked to a promoter and a polyadenylation sequence; and (d) a fourth vector containing a gene of interest, wherein said gene of interest is operably linked to a promoter and an HIV packing sequence necessary to package HIV RNA into HIV virions;

wherein the first vector, second vector and third vector, when expressed in combination, form a pseudotyped virion containing an envelope protein other than the HIV env protein around an HIV capsid; and wherein said at least first, second, third and fourth vectors do not contain a sufficient number of nucleotides to encode the HIV gag, env and pol proteins on a single vector; and wherein said first, second and third vectors do not contain nucleotides of the HIV genome, referred to as the HIV packaging segment, between the 5' major splice donor and the gag gene sufficient to effectively package HIV RNA; and wherein said at least first, second, third and fourth vectors, when expressed in combination, do not form a replication competent virus.

11. The vectors of claim 4, wherein at least one vector is a retroviral vector.

* * * * *

UNITED STATES PATENT AND TRADEMARK OFFICE
CERTIFICATE OF CORRECTION

PATENT NO : 5,981,276
DATED : November 9, 1999
INVENTOR(S) : Joseph G. Sodroski et al.

It is certified that error appears in the above-identified patent and that said Letters Patent is hereby corrected as shown below:

Col. 15, line 3
after "vector," insert -- containing--.

Col. 15, line 36
replace "or"
with --of--.

Col. 16, line 57
replace "or"
with --of--.

Col. 15, line 10
replace "HIE"
with --HIV--.

Signed and Sealed this

Twenty-fourth Day of October, 2000

Attest:

Q. TODD DICKINSON

Attesting Officer                    Director of Patents and Trademarks